(12) United States Patent
Bush et al.

(10) Patent No.: US 7,840,283 B1
(45) Date of Patent: Nov. 23, 2010

(54) BIPOLAR SCREW-IN LEAD

(75) Inventors: Mary Elizabeth Bush, Santa Clarita, CA (US); Rolf Hill, Jarfalla (SE); Steven R. Conger, Agua Dulce, CA (US); Olof Stegfeldt, Alta (SE)

(73) Assignee: Pacesetter, Inc., Sylmar, CA (US)

( * ) Notice: Subject to any disclaimer, the term of this patent is extended or adjusted under 35 U.S.C. 154(b) by 387 days.

(21) Appl. No.: 11/534,153

(22) Filed: Sep. 21, 2006

(51) Int. Cl.
  *A61N 1/05* (2006.01)
(52) U.S. Cl. .......................................... 607/127
(58) Field of Classification Search ............... 607/120, 607/127
  See application file for complete search history.

(56) References Cited

U.S. PATENT DOCUMENTS

| | | | |
|---|---|---|---|
| 3,737,579 A | 6/1973 | Bolduc | |
| 4,046,151 A | 9/1977 | Rose | |
| 4,146,036 A | 3/1979 | Dutcher et al. | |
| 4,233,992 A | 11/1980 | Bisping | |
| 4,282,885 A * | 8/1981 | Bisping | 607/127 |
| 4,463,765 A | 8/1984 | Gold | |
| 4,550,737 A | 11/1985 | Osypka | |
| 5,152,299 A | 10/1992 | Soukup | |
| 5,575,814 A | 11/1996 | Giele et al. | |
| 5,658,327 A | 8/1997 | Altman et al. | |
| 6,298,272 B1 | 10/2001 | Peterfeso et al. | |
| 2002/0161423 A1 * | 10/2002 | Lokhoff et al. | 607/127 |
| 2004/0068312 A1 * | 4/2004 | Sigg et al. | 607/120 |

FOREIGN PATENT DOCUMENTS

WO  0057949  10/2000

* cited by examiner

*Primary Examiner*—George R Evanisko
*Assistant Examiner*—Michael D'Abreu

(57) ABSTRACT

An implantable active fixation lead includes an outer sheath, a protector member having a peripheral surface extending between its distal and proximal end surfaces with a helical groove formed in the peripheral surface, and a fixation helix integral with the outer sheath. The fixation helix includes a tip end engageable with body tissue and slidably engaged with the helical groove for relative translation and rotation. A longitudinal force on the lead firmly engages the protector member's distal end surface with the body tissue. With the fixation helix initially retracted proximally of the protector member's distal end surface and disengaged from the body tissue, upon application of torque to the outer sheath, the distal end surface of the protector member is moved proximally with respect to the fixation helix which, simultaneously, is extended distally beyond the distal end surface of the protector member to an extended position into engagement with the body tissue.

9 Claims, 8 Drawing Sheets

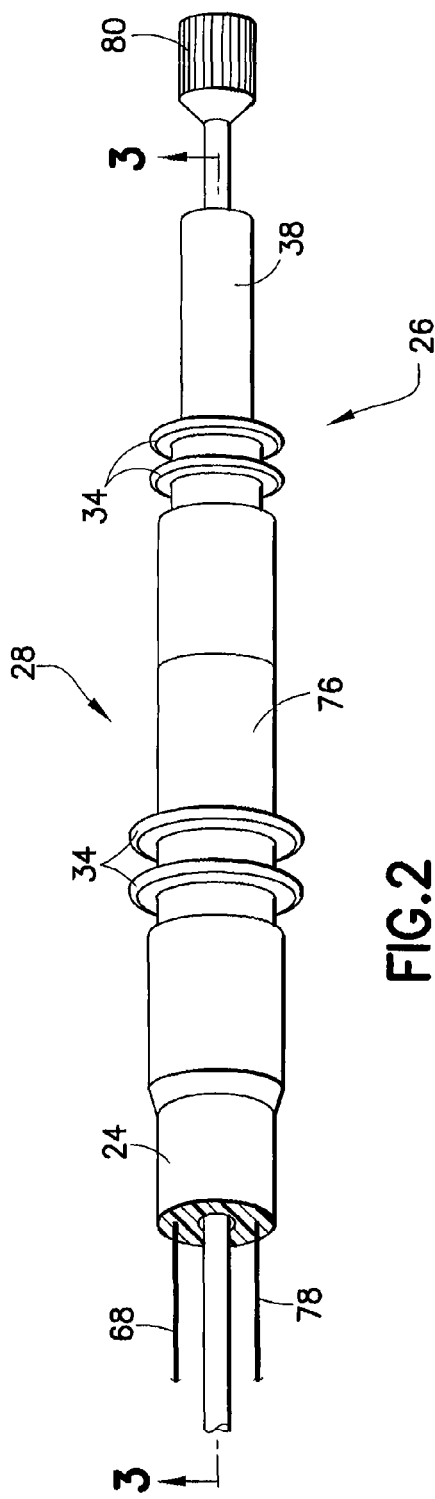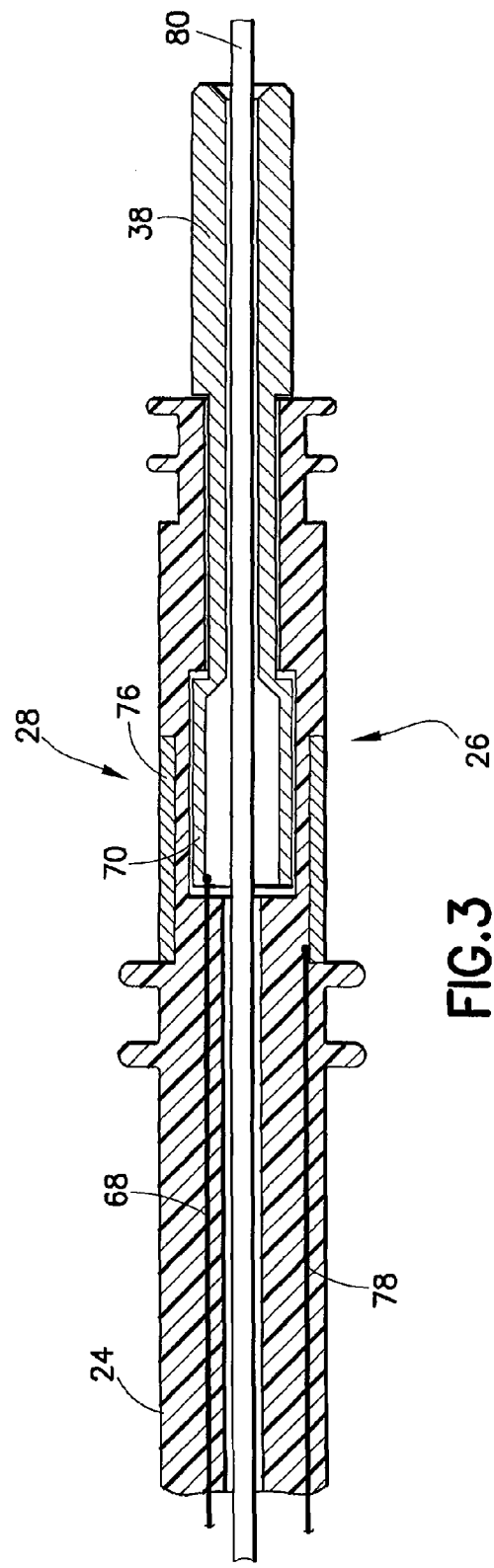

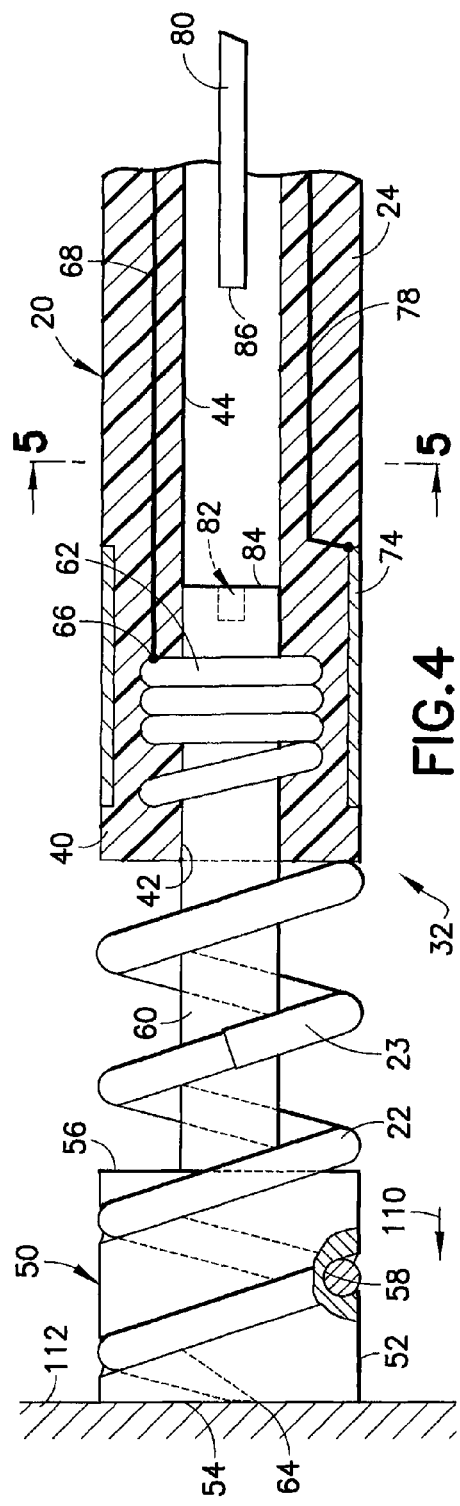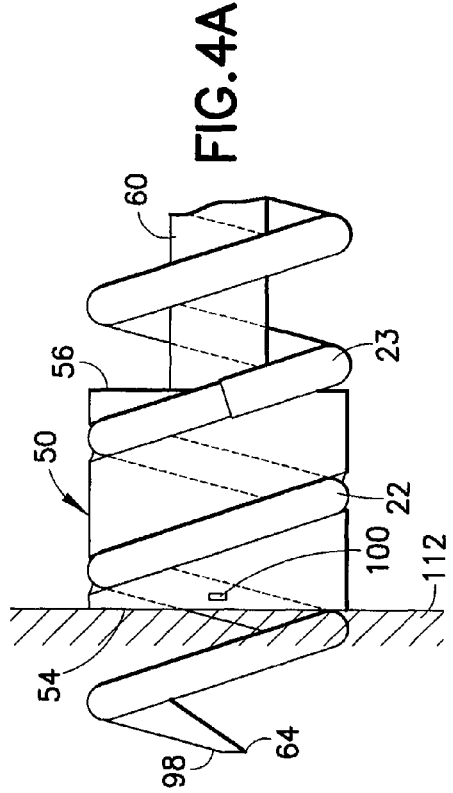

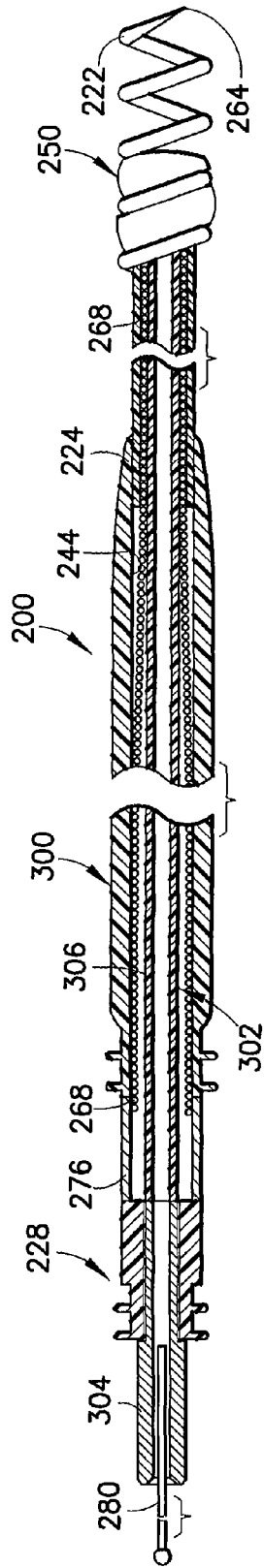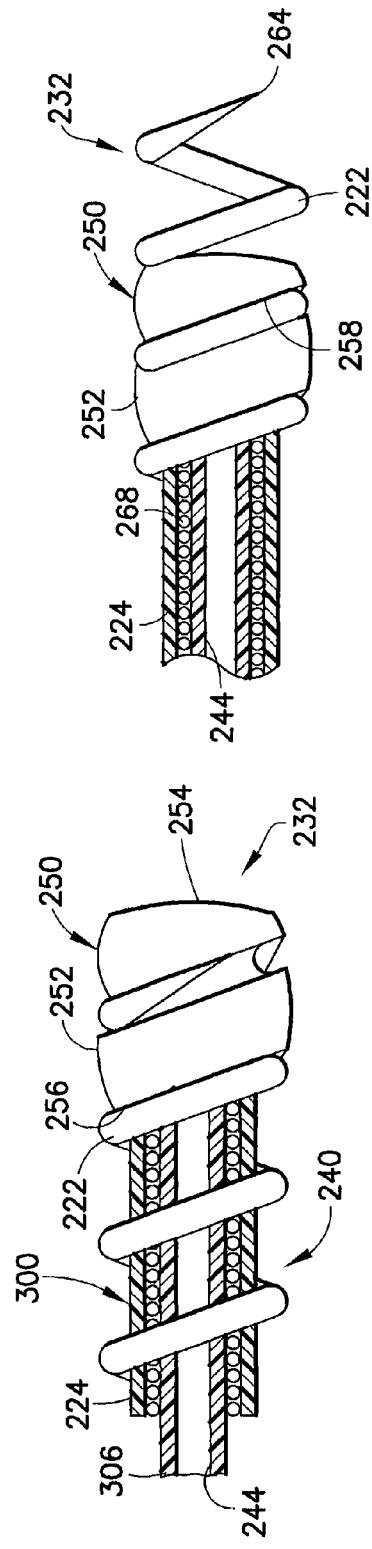

US 7,840,283 B1

BIPOLAR SCREW-IN LEAD

FIELD OF THE INVENTION

The present invention relates generally to implantable leads for medical devices that provide stimulating current to selected body tissue, for example, the heart, and more particularly, to an implantable stimulation lead having a bipolar active fixation electrode for pacing and sensing electrical activity in the heart. Still more particularly, the present invention relates to simplified lead constructions at the distal end that result in more efficient lead delivery with a lead of minimized diameter.

BACKGROUND OF THE INVENTION

Implantable cardiac stimulation and sensing devices are well known in the art. Such stimulation devices may include, for example, pacemakers or defibrillators. These devices are generally implanted in an upper portion of the chest beneath the skin of a patient within a surgically-created subcutaneous pocket.

Screw-in leads are notoriously costly and complex and have a lot of variation in performance. These characteristics are built into the lead because of the desire to shield the veins and tricuspid valve from the fixation helix during lead insertion. Many mechanisms have been employed for extending and retracting the helix, including a screwdriver-tipped stylet and a rotatable inner conductor attached to the helix. Because of the complexity of these various mechanisms, the leads that employ them are costly, complex, and subject to variable performance.

Currently-used active fixation transvenous cardiac leads are designed to utilize one of the following types of fixation approaches along with their recognized drawbacks:
1. "exposed fixed" helix; during insertion, the exposed fixed helix can be traumatic to vasculature and the tricuspid valve;
2. "fixed helix with a protective coating" wherein the exposed helix is coated with a dissolving substance, e.g. mannitol or polyethylene glycol (PEG); when the protective substance is dissolved, a fixed exposed helix, remains. Unfortunately, if the coating dissolves prematurely or if the lead needs to be removed and reinserted, the resulting lead continues to exhibit the same issues as No. 1 above;
3. the "rotating pin" extendable-retractrable helix which is retracted within the lead's distal housing until the helix is intended to be extended and fixated (that is, screwed) into the heart tissue. With this type of helix, the connector pin is rotated to rotate the conductor coil to rotate and extend the helix out of the lead's tip and screw it into the tissue. A major advantage of this helix extension/retraction approach is that it can be relatively easily positioned at almost any site in the right atrium (RA) and right ventricle (RV). A major disadvantage of this approach is that a large diameter, stiff protective header is used to house the helix during lead insertion, which causes the lead to be stiffer and larger diameter and/or the helix to be smaller diameter than would otherwise be optimal.
4. The "screwdriver stylet" extendable-retractable helix system is configured such that the wire stylet has a screwdriver tip at its distal end that engages into a slot at the proximal base of the helix electrode, and which then is used to screw the helix out in a one-to-one rotating ratio which is a very positive benefit; however, this design requires stocking specialized stylets.

It was in light of the foregoing known apparatus and techniques that the present invention was conceived and has now been reduced to practice.

SUMMARY

An implantable active fixation lead includes an outer sheath, a protector member having a peripheral surface extending from a distal end surface to a proximal end surface with a helical groove formed in the peripheral surface, and a fixation helix integral with the outer sheath. The fixation helix includes a tip end engageable with body tissue and slidably engaged with the helical groove for relative translation and rotation. A longitudinal force on the lead firmly engages the protector member's distal end surface with the body tissue. With the fixation helix initially retracted proximally of the protector member's distal end surface and disengaged from the body tissue, upon application of torque to the outer sheath, the fixation helix is extended distally beyond the distal end surface of the protector member to an extended position into engagement with the body tissue.

The present invention provides a simplified technique for ensuring that the veins and valves are protected from the helix during implant without the high cost and performance problems of the past. It also allows for the overall lead to be very small in diameter, preferably about 4 Fr.

The fixation helix has approximately the same or slightly larger diameter than the outer lead body. The anode ring has a groove for accommodating the helix. Although the helix is exposed to the body during implant, the valve and veins are protected because of the close fit between the helix within the anode ring groove in the retracted state.

An advantage gained by the invention as compared with known prior art is the ability to affix the helix to body tissue in one motion instead of requiring a first step of retracting the protective core to expose the helix and a second step of screwing in the helix, although this latter pair of operations may also be performed, if desirable.

Another advantage of the present invention is provided in the event a stylet is used: the stylet can be held fixed, while rotating the lead body over it during the entire fixation process, helping to stabilize the lead against the tissue in the desired location and to keep the lead rotating on its axis when screwing the helix into the tissue. By contrast, in the known prior art, once a protective core is retracted from the helix and the protective core has reached its limit of travel, the lead can no longer rotate with respect to the screwdriver stylet, and the stylet would have to be replaced with a non-screwdriver stylet, or the lead and stylet would have to rotate together, thus removing the advantage of keeping the lead rotating on its axis, or some other mechanism would need to be designed to make it a workable concept.

Another advantage of the invention is that no specialized stylet is required to expose the helix. This is a clear clinical and marketing benefit, saving time in having to switch stylets during a procedure and/or logistics of having to stock various stylets.

A preferred design of the invention takes advantage of short cathode to anode spacing (that is, closer helix to ring spacing) which is useful for far-field signal reduction. The helix may be insulated with parylene, silicone, PTFE, or other insulative coating over most of its length, with only a small portion, preferably the most distal tip, exposed to act as an electrode. The inner assembly is preferably closed and has a stylet slot at the inner distal end and may contain steroid at the outer distal tip.

By using a protector member that can rotate with respect to the rest of the lead but that can be made to stand still with respect to the heart when the lead tip is against the heart wall, the fixation helix can be automatically exposed when rotating the complete lead, engaging the helix with the tissue and screwing it in. To put this concept into practice, the surface of the protector member that is in contact with tissue can be made of a material having high friction with the tissue. Alternatively or additionally, it may have features such as a roughened surface, raised bumps, or recessed dimples, or may have a fabric such as PTFE mesh on its surface. Fabric may also improve acute and chronic electrode stabilization. Force is applied by the protector member to the heart to grip the tissue so that the protector member does not rotate when rotating the lead body. Optionally, a stylet may be used to apply additional force to press the protector member against the heart. The material that the stylet contacts may be one such as silicone that provides friction between it and the stylet. The stylet would not require a specialized tip such as a screwdriver blade, although in some non-preferred embodiments, one could be used and may be desirable.

In another instance, to extend and retract the helix, the outer assembly is rotated while stabilizing the inner assembly by holding the lead connector pin fixed. The helix serves as the cathode and is coupled to the lead connector ring in a typical bipolar connector. Although the lead connector ring is normally the anode in an IS-1 standard connector, in this case, the current generator is of a type wherein the ring can be programmed as the cathode. A screwdriver tipped stylet may be used to prevent rotation of the inner conductor while rotating the outer conductor, and to aid in torqueability for placing the lead, which may be important for the preferred diameter of 4 Fr. This stylet may be temporarily attached to the connector pin.

Other optional features of the invention include having more than one electrode, short electrode spacing between distal helix electrode and proximal electrode, adding one or more defibrillation electrodes, having all portions of the lead fixed with respect to each other except the protector member, providing steroid elution from the protector member, allowing mapping prior to fixation, having an essentially isodiametric lead body, downsizing the lead to fit through a 4 Fr introducer, minimizing manufacturing cost, minimizing the length of the rigid distal section, providing an X ray marker in the protector member, and providing some device, such as a stop or a tether, to prevent the protector member from falling out of the helix, off the end of the lead, and into the body.

It is preferred, but not required, that the stylet lumen lie on the central axis of the lead. For a bipolar lead, this can be achieved by using coaxial conductors, which may also be co-radial. Other lead body structures are possible for keeping the stylet lumen on the same axis as the lead. Alternatively, an off-center lumen may be provided by using an off-center coil conductor as one conductor and a cable conductor as a second conductor.

If it is desired to remove or reposition the lead within a cardiac chamber, most clinicians would probably consider it unnecessary to advance the protector member into the helix. However, in the event that this is desirable, a screwdriver or other mechanism could be used. If the lead is removed and it is desired to reinsert it, it would be necessary to advance the protector member. This could be done using a screwdriver stylet; alternatively, since the lead would be out of the body, a method and mechanism could be provided for advancing the protector member from the distal end.

One special feature of the invention, then, is the provision of a novel implantable stimulation lead having a bipolar active fixation electrode for pacing and sensing electrical activity in the heart.

Another feature of the present invention is the provision of a simplified distal end lead construction which results in more efficient lead delivery with a lead of minimized diameter.

Still another feature of the present invention is the provision of such a distal end lead construction for which a fixation helix is of the same diameter or of a larger diameter than the endocardial lead body;

Yet another feature of the present invention is the provision of such a distal end lead construction for which the fixation helix is electrically and mechanically coupled to a ring connector contact of a bipolar or multipolar connector.

Yet a further feature of the present invention is the provision of such a distal end lead construction for which the fixation helix is of the same diameter or of a larger diameter than that of a ring electrode.

Yet another feature of the present invention is the provision of such a distal end lead construction including a protector member having an outer surface with a helical groove and a fixation helix including a tip end engageable with the body tissue and slidably engaged with the helical groove for translation and rotation relative thereto for which, with a longitudinal force applied to the lead to firmly engage the distal end surface of the protector member with the body tissue and with the fixation helix initially retracted proximally of the distal end surface of the protector member and out of engagement with the body tissue, upon application of torque to the outer sheath, the distal end surface of the protector member is moved proximally with respect to the fixation helix which, simultaneously, is extended distally beyond the distal end surface of the protector member to an extended position into engagement with the body tissue.

Yet another feature of the present invention is the provision of such a lead construction which provides the ability to affix the helix to tissue in one motion instead of requiring a first step of retracting the protective core to expose the helix and a second step of screwing in the helix.

Still another feature of the present invention is the provision of such a lead construction for which, if a stylet is used, the stylet can be held fixed, rotating the lead body over it during the entire fixation process, helping to stabilize the lead against the tissue in the desired location and to keep the lead rotating on its axis when screwing the helix into the tissue.

Yet a further feature of the present invention is the provision of such a lead construction requiring no specialized stylet to expose the helix, being a clear clinical and marketing benefit, saving time in having to switch stylets during a procedure and/or logistics of having to stock various stylets.

Still another feature of the present invention is the provision of such a distal end lead construction for which a ring electrode has a screwdriver stylet slot.

Still a further feature of the present invention is the provision of such a distal end lead construction including an outer assembly, further including, in combination, an outer sheath and the fixation helix including a tip end for engaging the body tissue and being slidably engaged with the helical groove of the protector member for translation and rotation relative thereto and an inner assembly, further including, in combination, a holding pin at the proximal end of the lead fixed to the protector member via an intermediate member, the inner assembly extending through a lumen of the outer assembly such that torque applied to the outer assembly while holding fixed the inner assembly advances the tip end of the fixation helix distally beyond the distal end surface of the protector member to an extended position in engagement with the body tissue.

Yet another feature of the present invention is the provision of such a distal end lead construction including an outer assembly including, in combination, an outer sheath and a fixation helix integral with a distal end of the outer sheath with a tip end for engaging the body tissue and being slidably engaged with the helical groove of the protector member for translation and rotation relative thereto and an inner assembly further including, in combination, a holding pin at the proximal end of the lead fixed to the protector member via an intermediate member, the inner assembly extending through a lumen of the outer assembly such that, with the lead introduced into the body, in one instance, while holding fixed the inner assembly, applying torque to the outer assembly to extend the tip end of the fixation helix distally beyond the distal end surface of the protector member to an extended position and, thereafter, while applying a longitudinal force to both the inner assembly and the outer assembly, applying torque to both the inner assembly and the outer assembly to advance the tip end of the fixation helix into engagement with the body tissue and, in another instance, while applying a longitudinal force to the lead to firmly engage the distal end of the lead with the body tissue, and while holding fixed the inner assembly, applying torque to the outer assembly to extend the tip end of the fixation helix distally beyond the distal end surface of the protector member to an extended position in engagement with the body tissue.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate some of the embodiments of the invention, and together with the description, serve to explain the principles of the invention in general terms. Like numerals refer to like parts throughout the disclosure.

BRIEF DESCRIPTION OF THE DRAWINGS

FIG. 2 is a detail perspective view of a proximal end of the lead illustrated in FIG. 1;

FIG. 3 is a cross section view taken generally across line 3-3 in FIG. 2;

FIG. 4 is a detail longitudinal partial cross sectional view of the distal end of the lead illustrated in FIG. 1 and presenting a fixation helix in an initially retracted, protected position;

FIG. 4A is a detail side elevation view of a portion of the distal end of the lead illustrated in FIG. 4 and presenting the fixation helix in an extended position in engagement with body tissue;

FIG. 11 is a longitudinal cross section view of a modified lead embodying the invention;

FIG. 12 is a detail side elevation view illustrating the distal end portion of FIG. 11 and presenting a fixation helix in an initially retracted, protected position;

FIG. 12A is a detail side elevation view similar to FIG. 12A and presenting the fixation helix in an extended position for engagement with body tissue.

DETAILED DESCRIPTION OF THE PREFERRED EMBODIMENTS

Figure 1:
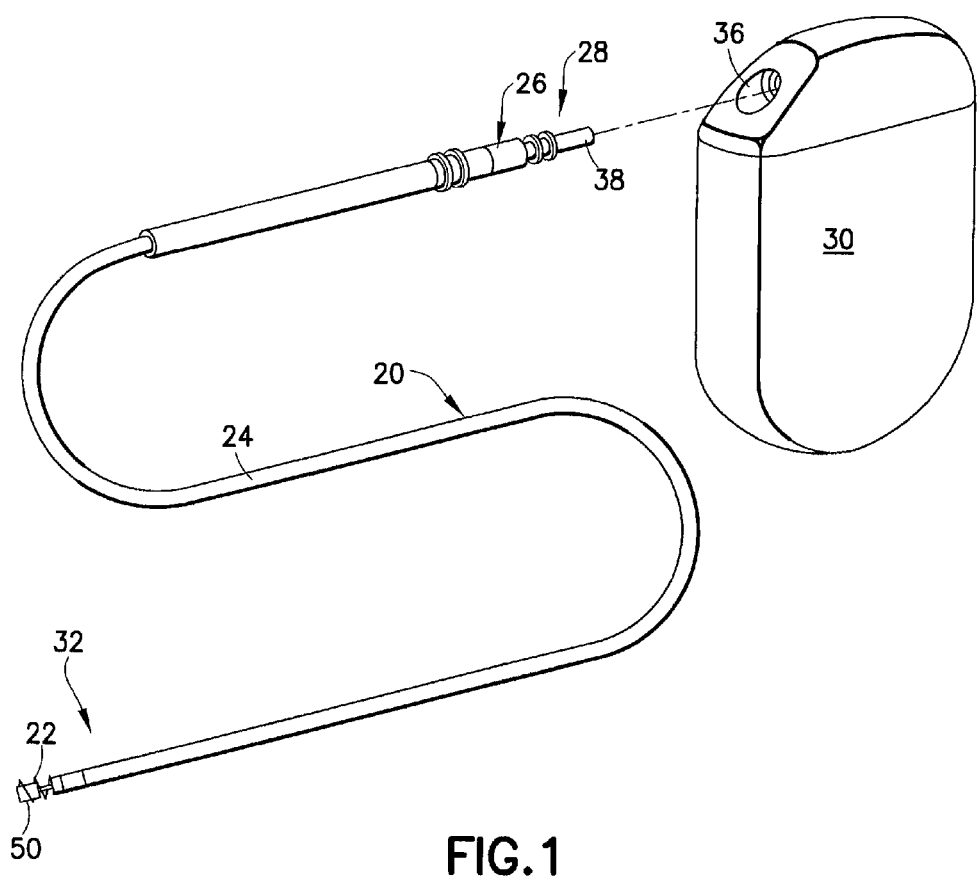
FIG. 1 is a perspective view of an implantable lead embodying the invention in combination with a stimulating device such as a pacemaker.

Referring to FIG. 1, there is shown a diagrammatic perspective view of an endocardial lead 20 incorporating features of the present invention. Although the present invention will be described with reference to the embodiments shown in the drawings, it should be understood that the present invention can be embodied in many alternate forms or embodiments. In addition, any suitable size, shape or type of elements or materials could be used. The lead 20 is attached to body tissue such as an interior wall of a heart by means of a fixation helix 22 at the distal end 32 for firmly engaging the tissue of the heart. Historically, the most successful fixation mechanism for pacing and ICD leads has been in the form of a screw-in fixation helix that can also serve as a helix electrode. This allows for the active fixation of a pacemaker lead in the myocardium, as well as for the acute removal if pacing and sensing parameters are not optimal.

Lead 20 further comprises a protector member 50 for aiding implantation, as will be described in detail below. The fixation helix 22 is coupled via a conductor 68 (shown in FIG. 2) to a lead connector 26 at a proximal end 28 of lead 20, to which can be attached a suitable stimulation device such as a pacemaker 30 so as to be coupled to the current generating and sensing circuits within the pacemaker. An outer sheath 24 comprising biocompatible material such as silicone electrically insulates the conductor 68.

As seen in FIGS. 2 and 3, lead connector 26 includes sealing rings 34 for sealing the connector cavity of the pacemaker against the entry of body fluids.

Turning now to FIG. 4, the distal end 32 of the lead 20 is seen to include an electrically insulative tubular housing 40, which is the extreme distal end of the outer sheath 24, defining an opening 42 that communicates with a proximally extending lumen 44.

A generally cylindrical protector member 50 that preferably is composed of electrically insulative material has a peripheral surface 52 extending from a distal end surface 54 to a proximal end surface 56 with a helical groove 58 formed in the peripheral surface. The protector member 50 further includes an integral stem 60 extending proximally away from the proximal end surface 56 and slidably received within the lumen 44 of the outer sheath 24. The fixation helix 22, which may be made of a platinum-iridium alloy, for example, has a proximal end 62 which is mechanically fixed with respect to (herein after referred to as "integral with") the distal end of the outer sheath 24. The fixation helix 22 includes a sharp tip end 64 adapted to pierce the body tissue and sharpened to an orientation to avoid inadvertently catching on body tissue as the lead is advanced into the body. The fixation helix 22 is slidably engaged with the helical groove 58 for translation and rotation relative to the protector member 50. Preferably, at least a portion of the fixation helix extending proximally of the protector member in the protected position, as illustrated in FIG. 4, has an insulative covering 23 thereon.

Figure 5:
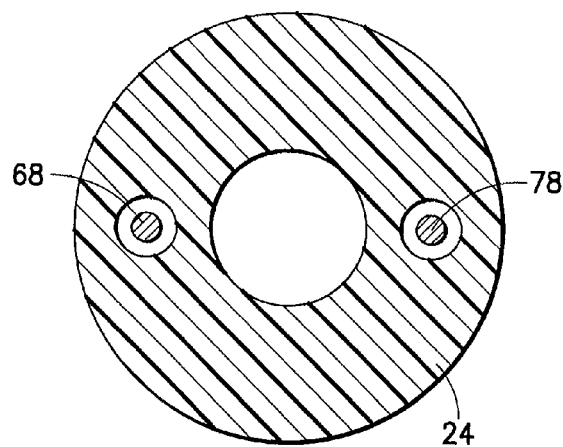
FIG. 5 is a cross section view taken generally across line 5-5 in FIG. 4.

In a well known manner, the fixation helix 22 serves as a fixation device to securely anchor the distal end of the lead 20 relative to the tissue to be stimulated and/or sensed and may further serve as an electrically conductive contact element for transmitting electrical current both for stimulation and for sensing. In its latter function, the fixation helix 22 may be called a helix electrode and is part of an electrode assembly connected to a distal end 66 (FIG. 4) of a conductor 68, the proximal end of which is received on and crimped or welded into engagement with a distal end portion 70 of the connector pin 38 (FIG. 3). FIG. 5 is a cross section view taken generally across line 5-5 in FIG. 4. While conductor 68 is illustrated as a cable, it could certainly be in the form of a coil.

A second electrode 74 (FIG. 4), illustrated as a ring electrode, is located proximally of the helix electrode 22, and a second connector contact 76 is located at the proximal end of the lead 20 electrically and mechanically coupled to the second electrode 74. A second conductor 78 (FIGS. 3 and 4) extends between the proximal and distal ends of the lead 20 within the outer sheath 24 for transmitting the electrical current between the second electrode 74 and the second connector contact 76. Again, as with conductor 68, while conductor 78 is illustrated as a cable, it could certainly also be in the form of a coil.

Figures 6, 7:
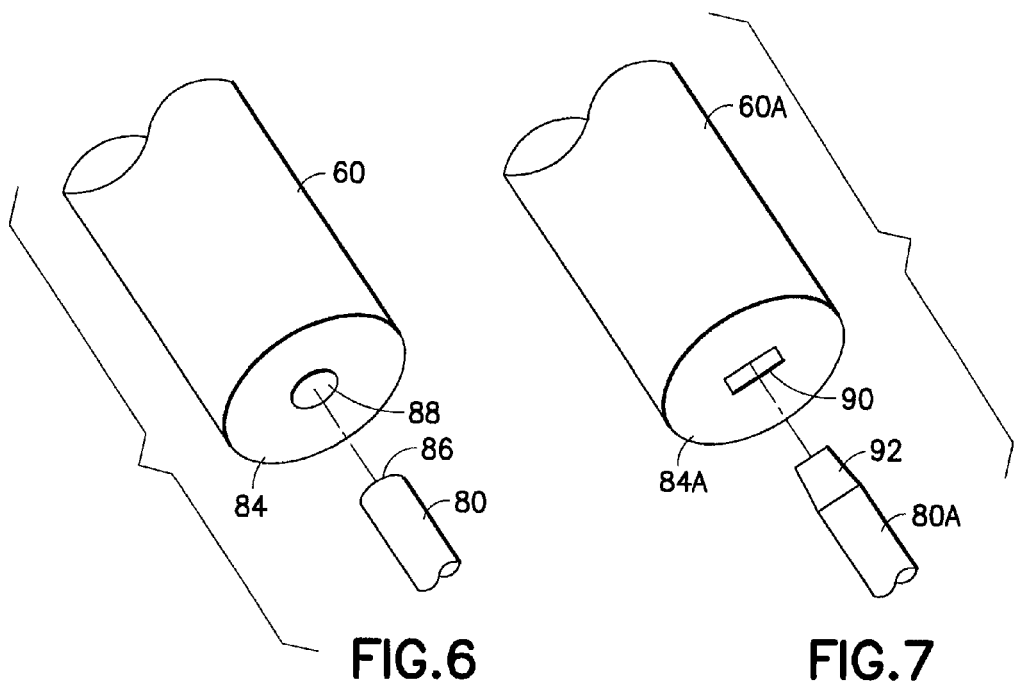
FIG. 6 is a detail perspective view illustrating an integral stem of a protector member of the invention with one form of stylet engaging member.
FIG. 7 is a detail perspective view illustrating a modified integral stem of the protector member of the invention with another form of stylet engaging member.

A stylet 80 may be used to support the lead 20 during the implanting and fixation procedure and, for example, may be used to apply additional force to press the protector member 50 against the body tissue. The material that the stylet contacts may be one such as silicone that provides friction between it and the stylet. For this purpose a stylet engaging member 82 (FIG. 4) is provided on a proximally facing portion 84 of the stem 60 of the protector member, specifically, capable of reception by a distal tip 86 of the stylet received through the lumen 44 of the outer sheath 24. The stylet engaging member 82 generally illustrated in FIG. 4 may be a simple blind bore 88 (FIG. 6) formed into the proximally facing portion 84 without a requirement that the stylet have a specialized tip. This construction offers a clear clinical and marketing benefit, saving time in having to switch stylets during a procedure and/or logistics of having to stock various stylets. The stylet can be held fixed, rotating the lead body over it during the entire fixation process, helping to stabilize the lead against the tissue in the desired location and to keep the lead rotating on its axis when screwing the fixation helix 22 into the tissue. In the alternative, however, there may be occasions when it becomes desirable, viewing FIG. 7, for the stylet engaging member to have a specially shaped recess 90 in a modified proximally facing portion 84A for engageably receiving a mating distal tip engaging member 92 of a modified stylet 80A shaped, for example, like a flat-blade screwdriver.

Figure 8:
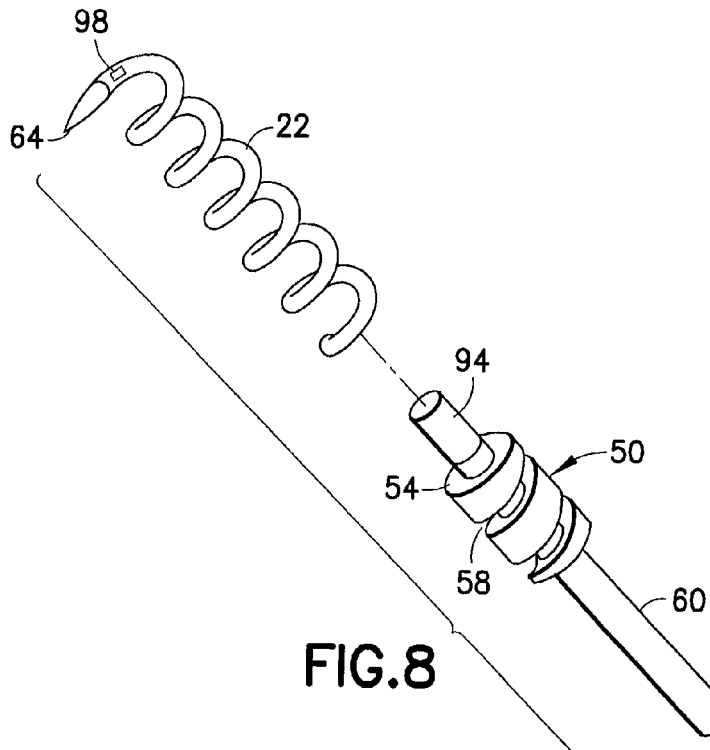
FIG. 8 is an exploded perspective view of components embodying the invention.
Figure 9:
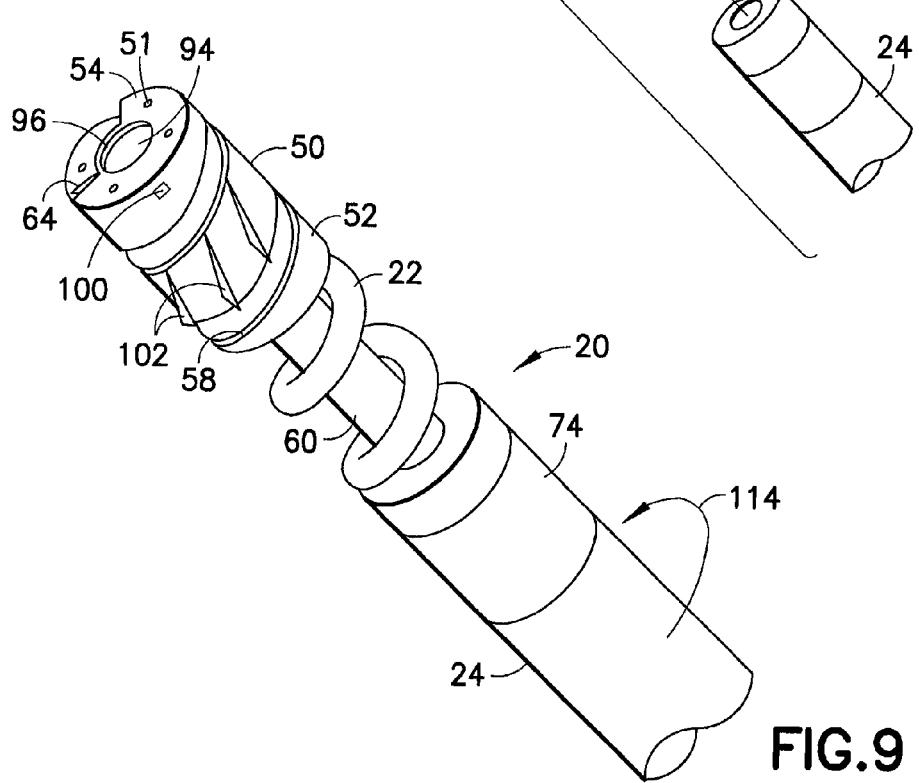
FIG. 9 is a detail perspective view of many of the components illustrated in FIG. 4.

Turning now to FIGS. 8 and 9, the protector member 50 may include steroid material in the form of a steroid plug 94 contained in a known manner in a recess 96 in the distal end surface 54. Additionally, the fixation helix 22 and the protector member 50 may each be provided with a fluoroscopic marker, 98 and 100, respectively, shown schematically in FIG. 4A. The markers can be in the form of barium sulfate loading or a metallic component. The fluoroscopic markers can be viewed when the lead 20 is being implanted to determine the position of the tip end 64 of the fixation helix 22 relative to the distal end surface 54 of the protector member 50.

Viewing FIG. 9, the protector member 50 also has one or more outwardly projecting fins 102 on the peripheral surface 52 oriented to prevent rotation of the protector member as it advances through a body vessel. The fins 102 also provide another function when the fixation position is reached, namely, they will then prevent or reduce the risk of having the protector member follow the distal end when turning the lead body. That is the case since the heart tissue not a smooth surface and tissue will also be against the peripheral surface 52 of the protector and not just on the distal end surface 54.

Figure 10A:
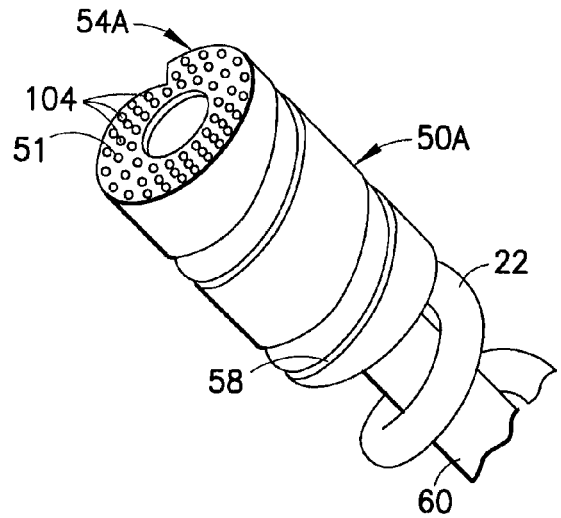
FIGS. 10A, 10B, and 10C are detail perspective views of an end portion of FIG. 9 illustrating various forms, respectively, of an end stabilizing feature for engagement with body tissue.
Figure 10B:
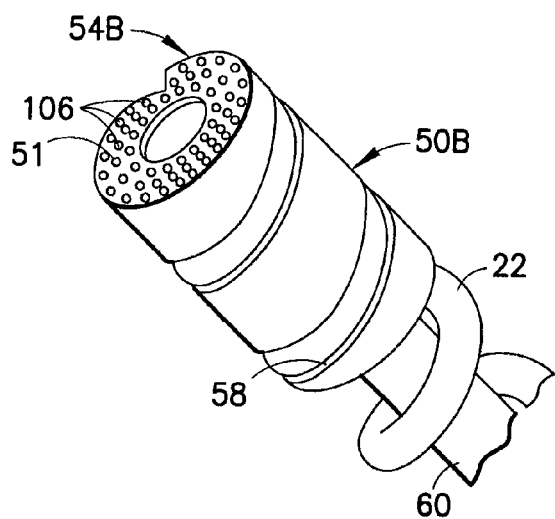
Figure 10C:
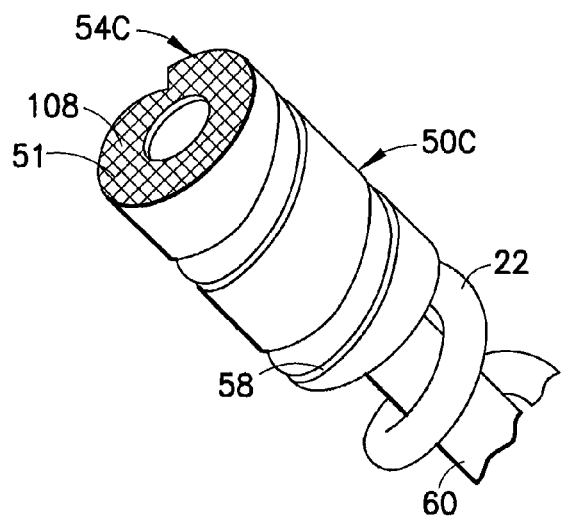

As will be explained below, the protector member 50 is designed to remain stationary against the body tissue when other portions of the lead 20 are rotated. For this purpose, the protector member includes an end stabilizing feature 51 on the distal end surface 54 for engagement with the body tissue. Stabilizing feature 51 can have a number of different constructions, one being a roughened surface for frictional engagement with the body tissue. For example, viewing FIG. 10A, on a modified protector member 50A, the roughened surface on a distal end surface 54A may be in the form of a plurality of raised bumps 104; viewing FIG. 10B, on a modified protector member 50B, the roughened surface on a distal end surface 54B may be in the form of a plurality of recessed dimples 106; or viewing FIG. 10C, on a modified protector member 50C, the roughened surface on a distal end surface 54C may be in the form of a mesh fabric 108.

The fixation helix 22 preferably has approximately the same diameter as the outer sheath 24 of the lead 20. In order to keep the helix diameter as large as possible while reducing lead diameter, for this invention, a customary header is replaced by the protector member 50 which is located within the fixation helix 22. The protector member 50 has the helical groove 58 for accommodating the fixation helix. Although the fixation helix is exposed to the body during the implanting procedure, the heart valve and veins through which the lead proceeds are protected because of the close fit between the fixation helix and the protector member 50 within the helical groove 58. Also as noted earlier, the tip end 64 of the fixation helix 22 is sharpened in an orientation to avoid inadvertently catching on body tissue. Further, because the fixation helix 22 is exposed even before retracting the protector member 50, the fixation helix can be used to map the body tissue prior to implantation of the lead 20.

Turning to FIG. 4, with the lead 20 constructed in the manner just described, a longitudinal force in the direction of an arrow 110 is applied to the lead 20 to firmly engage the distal end surface 54 of the protector member 50 with body tissue 112. The fixation helix 22 is initially in its protected condition with tip end 64 proximal of the distal end surface 54 and out of engagement with the body tissue. Then, upon application of torque to the outer sheath 24 as represented by an arrow 114 in FIG. 9, the fixation helix 22 is extended distally (viewing FIG. 4A) beyond the distal end surface 54 of the protector member 50 to an unprotected position into engagement with the body tissue 112.

Turning now to FIGS. 11-12A, in another embodiment of the invention, an implantable active fixation lead 200 engageable with body tissue includes a protector member 250, similar to the protector member 50, having a peripheral surface 252 extending from a distal end surface 254 to a proximal end surface 256 with a helical groove 258 formed in the peripheral surface. The lead 200 also includes an outer assembly 300 including, in combination, an outer sheath 224 and a fixation helix 222 integral with a distal end 240 of the outer sheath including a tip end 264 for engaging the body tissue. The fixation helix is slidably engaged with the helical groove 258 for translation and rotation relative to the protector member 250. The lead 200 further includes an inner assembly 302 including, in combination, a holding pin 304 at the proximal end 228 of the lead fixed to the protector member 250 via an intermediate member 306, the inner assembly extending through a lumen 244 of the outer assembly 300.

The lead is adapted for use with an implantable medical device such as the pacemaker 30 (FIG. 1) for transmitting electrical current between the proximal end 228 and an electrode at a distal end 232 of the lead. In this instance, the fixation helix 222 is a helix electrode and the outer sheath 224 comprises electrically insulative material. A connector ring contact 276 at the proximal end 228 of the lead 200 is mechanically and electrically coupled to the helix electrode 222, and a first conductor 268 extends between the connector ring contact 276 and the helix electrode 222 within the outer sheath for transmitting electrical current between the helix electrode and the connector ring contact.

Figure 13:
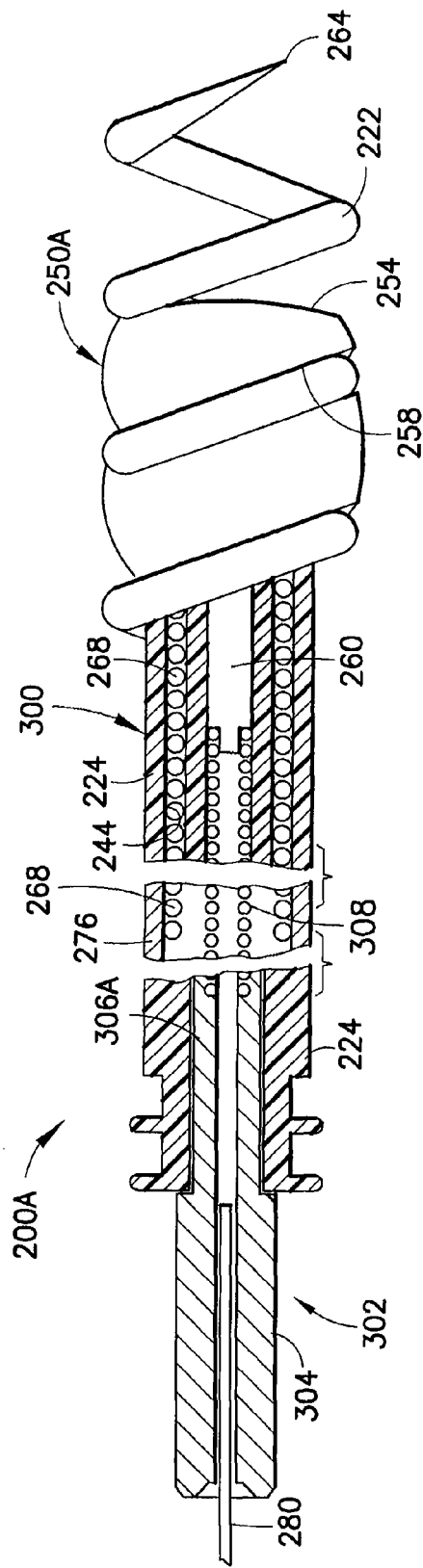
FIG. 13 is a longitudinal cross section view of another modified lead embodying the invention.

In another instance, turning now to FIG. 13, a modified lead 200A includes a protector member 250A, similar to the protector member 250 but being a second electrode proximal of the fixation helix. This combination includes a holding pin 304 being a connector pin and an intermediate member 306A which includes a second conductor 308 extending between the second electrode, that is, protector member 250A, and the connector pin 304. The second conductor 308 is electrically and mechanically coupled to a stem 260 of the protector member 250A.

With the construction of either FIGS. 11-12A or FIG. 13, torque applied to the outer assembly 300 while holding fixed the holding pin/connector pin 304 to hold the inner assembly 302 advances the tip end 264 of the fixation helix 222 distally beyond the distal end surface 254 of the protector member 250 or 250A to an extended position in engagement with the body tissue.

In another way of considering the possibilities of operating the unique lead of the invention, once the lead is introduced into the body, in one instance, while holding fixed the inner assembly 302, torque is applied to the outer assembly 300 to extend the tip end 264 of the fixation helix 222 distally beyond the distal end surface 254 of the protector member 250 to an extended position. Then, after performing this most recent step, while applying a longitudinal force to both the inner assembly and the outer assembly, torque is applied to both the inner assembly and the outer assembly to advance the tip end of the fixation helix into engagement with the body tissue.

In another instance, beginning with the helix 222 in its protected condition, while applying a longitudinal force to the lead to firmly engage the distal end surface 254 of the protector member 250 with the body tissue, and while holding fixed the inner assembly 302, in one continuous motion, torque is applied to the outer assembly to extend the tip end of the fixation helix 222 distally beyond the distal end surface of the protector member to an extended position in engagement with the body tissue.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable active fixation lead engageable with body tissue comprising:
   a lead body extending between a proximal and a distal end;
   a protector member connected to the lead body and having a peripheral surface extending from a distal end surface to a proximal end surface with a helical groove formed in the peripheral surface, wherein the proximal end surface of the protector member is located distal to the distal end of the lead body; and
   a fixation helix integral with the distal end of the lead body, the fixation helix including a tip end engageable with the body tissue and movably engaged with the helical groove for translation and rotation relative thereto;
   wherein the protector member has outwardly projecting fins on the peripheral surface oriented to prevent rotation of the protector member with respect to the helix as it advances through a body vessel and to hold fixed the protector member with respect to the body tissue as the fixation helix approaches the extended position into engagement with the body tissue.

2. The implantable lead of claim 1 wherein the protector member includes electrically insulative material.

3. The implantable lead of claim 1, wherein:
   the lead body defines a lumen; and
   the protector member includes an integral stem extending proximally away from the proximal end surface and slidably received within the lumen.

4. The implantable lead of claim 1 wherein the fixation helix has an outer diameter the same as that of the protector member and of the lead body.

5. The implantable lead of claim 1 wherein the fixation helix has an outer diameter no smaller than the diameter of the lead.

6. The implantable lead of claim 1 wherein the tip end of the fixation helix is sharpened to an orientation to avoid inadvertently catching on body tissue.

7. The implantable lead of claim 1 wherein the protector member includes steroid material.

8. The implantable lead of claim 1 wherein the distal end surface of the protector member includes an end stabilizing feature for engagement with the body tissue.

9. The implantable lead of claim 1 including a stylet engaging member on a proximally facing portion of the protector member capable of reception by a distal tip of a stylet received through a lumen of the lead body.

* * * * *